United States Patent [19]
Szlema et al.

[11] Patent Number: 5,772,620
[45] Date of Patent: Jun. 30, 1998

[54] HAND AND WRIST JOINT ORTHOSIS

[75] Inventors: Ingeborg Szlema, Kempen; Dieter Brandt, Düsseldorf, both of Germany

[73] Assignee: Beiersdorf AG, Hamburg, Germany

[21] Appl. No.: 553,268

[22] PCT Filed: Aug. 10, 1994

[86] PCT No.: PCT/EP94/02655

§ 371 Date: Nov. 22, 1995

§ 102(e) Date: Nov. 22, 1995

[87] PCT Pub. No.: WO95/04507

PCT Pub. Date: Feb. 16, 1995

[30] Foreign Application Priority Data

Aug. 11, 1993 [DE] Germany .......................... 43 26 751.3

[51] Int. Cl.⁶ ...................................................... A61F 5/00
[52] U.S. Cl. .................................. 602/21; 128/878; 602/6
[58] Field of Search .............................. 602/5, 6, 20, 21; 128/878, 879, 881

[56] References Cited

U.S. PATENT DOCUMENTS

| 315,512 | 4/1885 | Kearns | 602/21 |
| 1,298,529 | 3/1919 | Maddox | 602/21 |
| 2,318,864 | 5/1943 | Jackson | 602/21 |
| 3,526,006 | 9/1970 | Beardmore | 602/21 X |
| 4,006,741 | 2/1977 | Arluck | 602/7 |
| 4,716,892 | 1/1988 | Brunswick . | |
| 4,782,825 | 11/1988 | Lonardo | 602/21 |
| 4,873,968 | 10/1989 | Finnieston et al. | 602/21 |
| 5,058,576 | 10/1991 | Grim et al. . | |
| 5,152,739 | 10/1992 | Grob . | |
| 5,205,812 | 4/1993 | Wasserman | 602/21 X |
| 5,415,623 | 5/1995 | Cherubini | 602/20 X |
| 5,415,624 | 5/1995 | Williams | 602/21 |

FOREIGN PATENT DOCUMENTS

9112665  3/1992  Germany .

*Primary Examiner*—Linda C. Dvorak
*Attorney, Agent, or Firm*—Friedrich Kueffner

[57] ABSTRACT

The hand and wrist joint orthosis is comprised of a supporting body (10) enclosing wrist joint and hand in a sleeve-like fashion and of a spoon-shaped rigid splint disposed on the inner wall area of the supporting body (10) supporting the hollow hand and making it possible for the hand to assume the so-called intrinsic-plus position, which splint, within the region of the phalanges and the metacarpal bones, possesses three splint sections bent aside towards each other with such angular positions relative to each other that angles of $\alpha=40°\pm5°$ dorsal extension in the wrist joint as well as of $\alpha 1$ and $\alpha 2$=each of $60°\pm5°$ palmar flexion are predetermined in the metacarpophalangeal joints and in the proximal interphalangeal joints are predetermined for the digits (FIG. 1).

14 Claims, 10 Drawing Sheets

HAND AND WRIST JOINT ORTHOSIS

BACKGROUND OF THE INVENTION

1. Field of the Invention

The invention relates to a hand and wrist joint orthosis for the treatment of tendovaginitis.

2. Description of the Related Art

From DE-U-17 61 705, a device for the immobilization of the human hand and digits is known, wherein the connection of a splint with a body is effected, whose configuration is such that the hand or the digits to be immobilized in each case are able to rest in a functional position on this body and in that, furthermore, the body is provided with perforations, e.g. slots which, if necessary, permit the attachment of special retaining means, paddings, etc., as well as an air access. According to this, a splint is connected with a body, in which case the splint possesses a configuration and, possessing the form of a dynamic hand splint, maintains the hand in the medical functional position. If the body, which is connected with the splint so as to form a unit, is given the shape of a predeterminable three-dimensional curve whose transversal curve of the hollow hand at the level of the metacarpophalangeal joint and does justice to the convergent course of the digits when the fist is closed and whose longitudinal curve is selected in such a way that the digits bear against the curved hand like tangents, in which case the digits are inevitably moved into the desired articular position, then an immobilization in a functional position can be achieved by a simple bending of the splint. The configuration and size of the body of the splint is chosen in accordance with a mean value of the order of magnitude of the hand(s) of adults as are encountered in nature so that a standard device for providing a hand with a splint that is to fit almost all hands and digits. Occurring minor differences in the size of the different hand are in this connection to be compensated in that the respective hand more or less engages around the surface of the device. However, on account of this it is not possible to support and fixate the metacarpophalangeal joints in the elongated digits at a flexion of from 70° to 80° since no accuracy of fit exists. To this is added the circumstance that the supporting body formed on one end of the splint is constructed in the form of a hollow body so that, when the splint is applied, the elongated digits of the hand grip around this hollow body which possesses an approximately circular cross-section. Because of this a clear angular fixation of the phalanges relative to each other is not ensured. The attachment of the splint on the forearm, wrist joint and digits is effected by the application of a bandage. In order to fixate one or several elongated digits of the hand, a complicated winding and routing of the bandage is called for. That is why the application of this hand splint is possible only through trained specialist staff. If the bandage is not perfectly wound and routed in a pressure-relieving manner when the hand splint is applied and fixated, constrictions and, with this, haemostases, may consequently result. Nor is a stable fixation possible for a prolonged period of time, which is due to the slackening of the tensile forces of the bandage.

DE-U-81 28 832 describes an elastic wrist joint bandage for optional application as elastic support or for the immobilization of the wrist joint; it is designed in such a way that a detachable splint is provided on the inner hand. However, this wrist joint bandage is in no way a dynamic hand splint for supporting the hand in the known medical functional position. The elongated digits of the fixated hand are freely movable when the wrist bandage is applied. The splint extends over a section of the forearm across the wrist joint up to the inner hand and its function is exclusively a supporting one.

From the U.S. Pat. No. 4,584,993, a cuff-like constructed bandage enclosing the carpus and wrist joint without the possibility of maintaining the hand in the medical functional position can be gathered. This wrist joint bandage does in no way make a fixation of the hand in the medical functional position possible. The metacarpophalangeal joints of the elongated digits cannot be supported in a flexion position of from 70° to 80°. After the wrist joint bandage has been applied, the elongated digits are freely movable.

Apart from wrist joint bandages for the optional use as support for the immobilization of the wrist joint according to DE-U-81 28 832.8 or wrist joint supports with the bandage enclosing the carpus and the wrist joint according to DE-A-3 910 318 or according to DE-U-88 11 364.7, in which exclusively a support of wrist joint is effected by means of a volar or dorsal splint and which, in the case of dislocations and distortions as well as in the case of arthroses of the carpus, are employed for the functionally caused immobilization, arm and wrist joint supports and splints are known in the most widely varied embodiments.

The orthosis for the lower arm and the hand for the relaxation and immobilization of the muscular insertions on the epicondylus radialis according to DE-U-91 12 665.7 is constructed in such a way that a splint accommodates the forearm and the hand volarly or dorsally, which, within the area of the wrist joint, possesses a flexion of approximately 5° to 10°, in which case the splint terminates spaced apart distally from the ulnar bend. Forearm and hand can be fixated on this splint by means of straps. With this orthosis it is intended to make a relaxed, slightly flexed position in the wrist joint and in the phalangeal joints possible and to ensure an immobilization of the muscular attachments which are responsible for the pain.

According to EP-A-0 039 323, a splint for the reduction and immobilization of digital and matacarpal fractures, as well as a method for the fabrication of this splint is known. This splint is comprised of a plastically deformable strip which, on its terminal areas, possesses at least one transverse portion for the fixation on the forearm, the strip, on its longitudinal borders, being provided with weakened portions which make a bending of the strip in its plane possible. This strip is preferably entirely surrounded with a covering of nonrigid material. By virtue of this construction, the splint can be readily imparted the anatomically correct configuration, but it does retain the desired shape. In order to bring the strip into the anatomically correct configuration, it has to be considered in this case that the axes of the digits depart from a transversally proceeding curve of the hand and, when the digits are bent aside, the axes no longer proceed paralell as they do in the extended position, but converge at the knob of the navicular bone. Thus the digit axes, setting out from a parallel position in the extended position of the digits when the digits are bent aside, constantly change their direction until they ultimately, with completely bent-aside digits, aim at the knob of the navicular bone.

An immobilization of the digits which have suffered a fracture cannot be carried out now in the extended position of the digits, but has to be effected in the medial digital position so that the tendons are extended and the fingers do not grow stiff. This imposes the condition that also the digit splint has to be brought into a position which corresponds to the respective medial flexural positions of the digit(s) to be immobilized. This splint allows for these anatomical facts and makes a bending of the strip in its plane possible, while the weakened portions of the strip on its two longitudinal margins makes it possible that the strip cannot merely be bent in its plane and rotated about its longitudinal axis, but that is can also be bent transversally to the longitudinal axis in its plane so that the longitudinal axis then represents a curve bent in two planes essentially twisted relative to each other, whereby it is intended to be ensured that the splint can, for each digit and each fracture, be brought exactly into a position which is adapted to the anatomical configuration and position of the digit(s).

For the treatment of inflammatory diseases of the tendons, in which predominantly the synovial sheaths and the gliding tissues are affected, splints are also employed, thus, inter alia, also a splint which has to be therapeutically classified as being between a plaster of paris bandage and the known wrist joint bandages with stabilizing elements. On the one hand, this splint does not possess the stabilizing effect of a plaster bandage and cannot be employed for the treatment of fractures. On the other hand, in the case of painful irritations of the synovial sheaths, it constitutes an excessive medical care, especially since the respective bandages are much less bulky and offer a substantially greater wearing comfort. While minor irritations of the synovial sheaths are treated with stabilizing wrist joint bandages, no suitable orthopaedic appliance is available for the therapy of a "genuine" tendovaginitis. These cases are customarily immobilized with a plaster bandage or a semi-rigid support bandage in the functional position, that is to say, the position of the hand and the position of the wrist joint are interconnected.

SUMMARY OF THE INVENTION

It is the object of the present invention to provide a dimensionally stable hand and wrist joint orthosis in conformity with the type in question, more particularly for the treatment of tendovaginitis, in which the wrist joint, the joints forming part of the metacarpophalangeal joints and the joints located in the direction of the central portion and between the phalanges (proximal interphalangeal joints) are also enclosed by the orthosis, in which, for the immobilization of the synovial sheaths, within the anterior termination of the orthosis, an additional fixation of the digits takes place and in which the incorporated splint predetermines the following angular positions:

Wrist Joint: Extension taking place 40° to the back of the hand (dorsal extension)

Metacarpophalangeal Joints: 60° flexion of the digits towards the palm (palmar flexion)

Proximal Interphalangeal Joints: 60° flexions of the digits towards the palm (palmar flexion), whereby a stabilization is intended to be achieved extending over a prolonged period of time.

In accordance with the present invention, a hand and wrist joint orthosis of a bandage-like supporting body is provided which, with the aid of closing tapes, can be fixed on the hand and on the wrist joint and into which a volar splint is incorporated in order to keep the hand in the functional position, more particularly for the treatment of tendovaginitis, wherein the orthosis is comprised of profile-sewn supporting body enclosing wrist joint and hand in a sleeve-like fashion which, with a section facing the digits, terminates so as to overlap the joints within the region of the phalanges and extends over the greater part of the digits, and of a spoon-shaped rigid splint disposed on the volar side in the inner wall area of the supporting body so as to support the hollow hand and making it possible for the hand to assume the so-called intrinsic-plus position, which, within the region of the phalanges and the metacarpal bones possesses three splint sections which are bent aside towards each other with such angular positions that the angles of $\alpha=40\pm5°$ dorsal extension in the wrist joint as well as of $\alpha 1$ and $\alpha 2$ each $60°\pm5°$ palmar flexion in the metacarpophalangeal joints and in the proximal interpahlangeal joint are obtained.

While conventional wrist joint orthoses terminate within the region of the metacarpus, such an orthosis constructed according to the invention includes the metacarpophalageal joints (MCP joints) as well as the proximal interphalangeal joints (PIP joints), in which case the orthosis fixates said joints in a functional position. For the immobilization of the synovial sheaths, a fixation of the digits is additionally provided on the anterior termination of the bandage-like supporting body of the orthosis.

The supporting body of the hand and wrist joint orthosis is profile-sewn; it assumes the appropriate functional position and is comprised of a padded, stiff fabric. In order to have a long lever on the forearm, the orthosis is provided with a long forearm sleeve. On the one hand, the orthosis extends decidedly further than the known orthoses and wrist joint supports; it terms so as to overlap the wrist within the region of the proximal phalanx. The anterior termination is chamfered while following the anatomical contour(s). The digits are fixated with the aid of an inelastic Velcro strip fastener utilizing VELCRO, i.e.,a hook and loop-type connection. This strip fastener and two fixation points are located on the anterior termination of the orthosis.

As stabilizing element, on the side of the hollow hand (on the volar side), a spoon-shaped splint supporting the hollow hand and permitting the so-called intrinsic-plus position to be assumed is integrated, which predetermines the desired angles of $40°\pm5°$ of an elastic located at the back in the longitudinal direction (dorsal extension) in the wrist joint, as well as a $60°\pm5°$ flexion of the digits towards the palm (palmar flexion) in the MCP and PIP joints. This splint is accommodated in a pocket with a strip fastener and can at all times be easily taken out in order to be able to effect a replacement of splints possessing a different construction. With this, a phasing out of medical care and a cleaning of the orthosis is possible.

Moreover, the splint located on the volar side possesses a good padding so as not to exert any pressure upon the blood vessels located on the hollow hand side, in which case this padding is preferably achieved by means of the material which is used for the fabrication of the pocket holding the splint.

The orthosis is closed laterally. In the putting-on aperture proceeding over the entire length of the orthosis, within the region of the forearm sleeve as well as the front hand portion, a textile insert of preferably highly elastic fabric with a thumb aperture is sewn in, whereby the putting on of the orthosis is facilitated and a closed appearance and thus an enhanced wearing comfort is provided. Within the area of the forearm as well as that of the hand, the orthosis is secured with opposedly disposed, wide, inelastic closing tapes which, by preference, are in the form of strip fasteners so that an adaptation to different arm widths and hand widths is possible.

It is particularly advantageous that the orthosis, owing to its constructional configuration, also encloses the MCP and PIP joints, in which case the joints are fixated in the predetermined angular position. The frontside fixation of the digits on the orthosis makes an immobilization of the synovial sheaths possible.

As a tendovaginitis splint, the orthosis according to the invention is suited for replacing the known permanent bandage for the treatment of tendovaginitis. Just like the plaster-based medical care, the orthosis is likewise engaging over the joints within the region of the proximal phalanx. Due to the special anatomical situation that the muscles which move the digits are located in the forearm and are connected by means of long tendons with the joint, which all pass through the "eye of the needle", the wrist joint, it does not suffice to exclusively immobilize the wrist joint only for the immobilization of the synovial sheaths. Only by the enclosure of the digits into the orthosis, an adequate immobilization is achieved. Following the classic plaster of paris treatment, the tendovaginitis orthosis immobilizes the wrist joint and the hand in the functional position. In the process, the wrist joint is fixated in a dorsal extension of 40°±5°. The MPC joints are brought into a palmar flexion of 60°±5°, likewise also, the PIP joints in the same way as the MCP joints.

The orthosis is preferably employed for the treatment of tendovaginitis, but it may also be employed in the case of severe distortions, after wrist joint operations, tendon operations, fractures of the radius and following the removal of plaster casts, i.e. the scope of application of the orthosis also extends to all follow-up or after treatments after surgical interventions. Also in the case of acute irritations as a result of navicular pseudoarthrosis, lunatomalacia and arthroses, the orthosis can be successfully made use of.

The orthosis is constructed in a therapeutically balanced fashion and brings wrist joint and hand into the optimal functional position. The wrist joint is stabilized and immobilized. The movement of the digits is eliminated. In addition, the orthosis retains its shape and acts continuously in a stabilizing manner over a prolonged period of time. Furthermore, the orthosis fits well and is deformable according to the individual requirements of the patient; it adapts to different forearm widths and widths of the hand. Moreover, the orthosis is anchored firmly on the forearm. An unwanted pressure on the blood vessels proceeding on the volar side is prevented.

The orthosis produces still further the following advantages:

The orthosis does not-chafe, causes no pressure sores, is not very bulky, possesses a low weight, is kind to the skin as well as permeable to air and steam. An unpleasant heat effect is avoided. Over and above that, the orthosis, in the event of a primary medical care, is quickly and simply adaptable to anatomical conditions; it can be easily put on and it is not readily stained and soiled and can be washed without any problem.

BRIEF DESCRIPTION OF THE DRAWINGS

Embodiment examples of the invention are described in greater detail in the following with the aid of the drawings. Thus

DESCRIPTION OF THE PREFERRED EMBODIMENTS

The hand and wrist joint orthosis 100 illustrated in FIGS. 1 to 6 is comprised of a profile-sewn, bandage-like supporting body 10 enclosing wrist joint and hand in a sleeve-like fashion with an upper supporting body portion 10a and a lower supporting portion 10b. The two supporting body portions 10a, 10b are interconnected within the area of the supporting body longitudinal side 10c, while the supporting body 10, within the region of its longitudinal side 10d, is constructed so as to be open while forming a slipping-on aperture extending over the entire length of the orthosis, in which case, however, this slipping-on aperture 11 is constructed so as to be closed with the aid of a textile insert 30.

The fixation of the orthosis 100 on forearm, wrist joint and hand is effected with the aid of two longitudinally variable closing straps or bands 40, 41, by preference of inelastic material with an alternately opposed or identical winding direction. These closing straps 40, 41 are expediently constructed in the form of strip fasteners. By means of the closing straps 40, 41, the two supporting body portions 10a, 10b of the supporting body 10 are held together so that, in the applied state of the orthosis 100, the supporting body 10 encloses the wrist joint, hand and forearm in a sleeve-like fashion.

At the one end, the supporting body 10 is designed so as to be open in order that a slipping-in aperture 13 be formed so that the orthosis can be drawn over the hand and the forearm.

The supporting body 10 of the orthosis 100 is provided with a sleeve 14 corresponding roughly to the length of the forearm so that the orthosis 100, in the applied state, extends over the entire forearm.

The supporting body 10, at its end facing away from the slip-in aperture 13, is provided with a section 12 engaging over the digits, which terminates within the region of the proximal phalanx.

Figure 2:
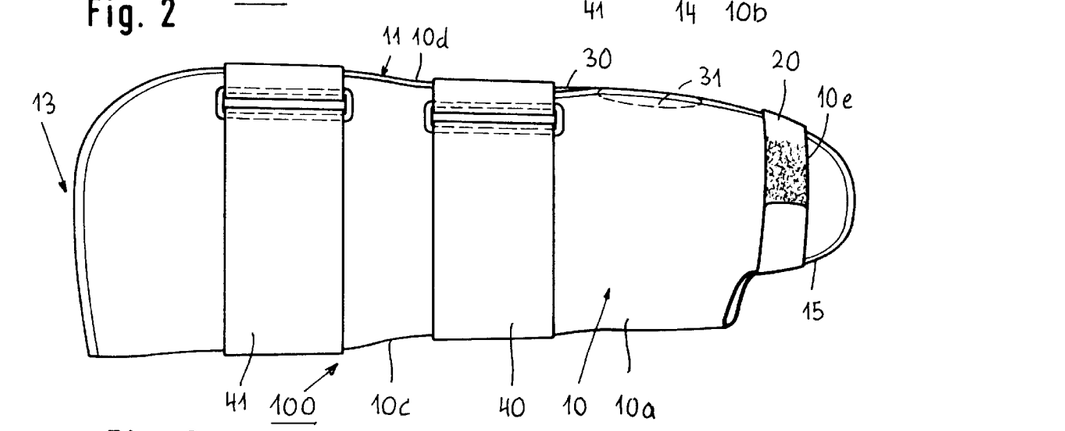
FIG. 2 shows the orthosis in a view from above.
Figure 3:
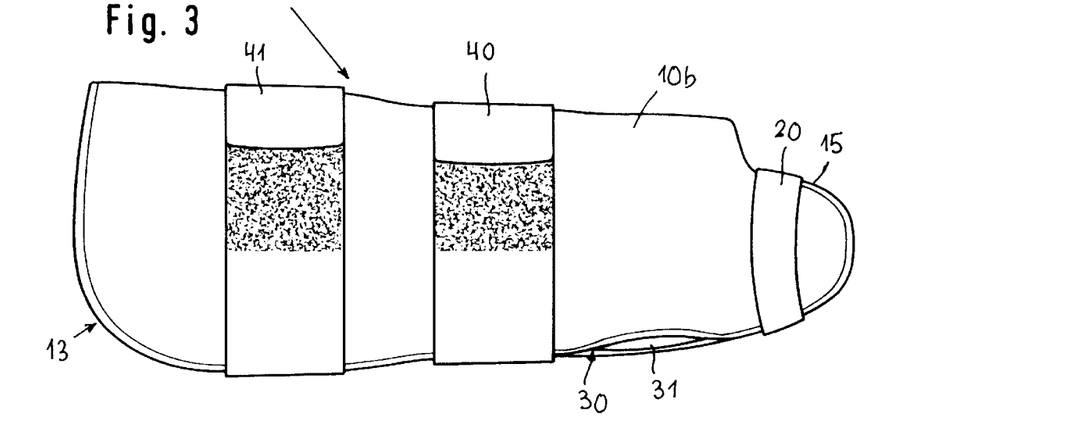
FIG. 3 shows the orthosis in a view from below.

The anterior termination 15 of the supporting body 10 is chamfered following the anatomical contour(s) of the digits and fitted with an unelastic band 20. The digits are fixated with the aid of this band 20, in which case the band 20 with its fixation points is located at the anterior termination 10e of the orthosis (FIG. 2). This inelastic band 20 for the fixation of the digits, according to one embodiment, possesses a predetermined, invariable length, whereas, however, also according to a further embodiment, this band 20 is constructed so as to be variable in its length. The two free ends of a thusly constructed band 20 are preferably closable with the aid of a strip fastener. Rim darts on band 20 prevent the band from pressing into the digital surfaces.

Figure 1:
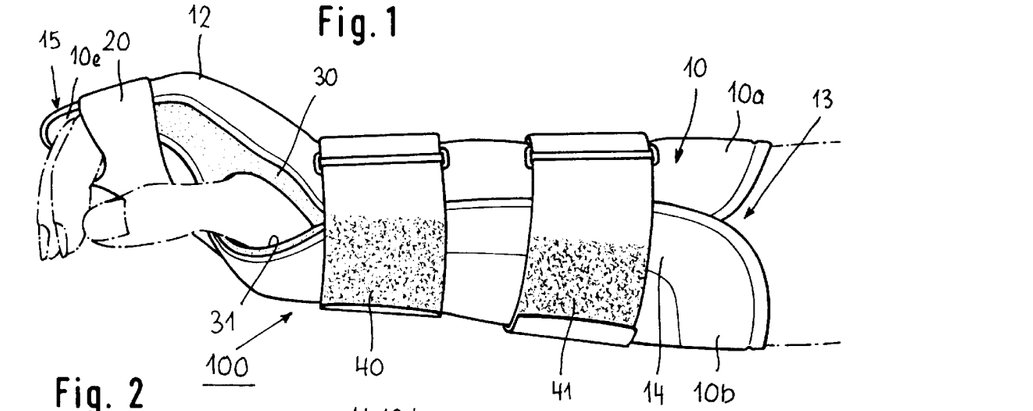
FIG. 1 shows in a diagrammatical side view the orthosis applied to the hand and wrist joint with a sleeve engaging over the forearm.

The textile insert 30 connecting the two supporting body portions 10a, 10b within the longitudinal lateral area 10d is comprised of a fabric having a sewn-in thumb aperture (FIG. 1). The fabric for this textile insert may be constructed so as to be rigid but also so as to be elastic. The digit fixation strap 20 should preferably be comprised of an inelastic fabric.

The supporting body 10 of the orthosis 100 is provided with a spoon-shaped splint 60 supporting the hollow hand and making it possible for the hand to assume the so-called intrinsic-plus position, which is disposed on the inner wall area of the supporting body. This splint 60 is comprised of a material possessing a high degree of inherent rigidity which, once it has received its configuration, cannot subsequently be deformed any more. By preference this splint 60 is comprised of a metallic material, while it is also possible for other materials to be employed. For enhancing the breathing activity and for avoiding a heat accumulation in the interior of the applied orthosis, this splint 60 in the form of a punched splint is provided with perforations 61 (FIGS. 8, 9 and 10).

Figures 8, 10:
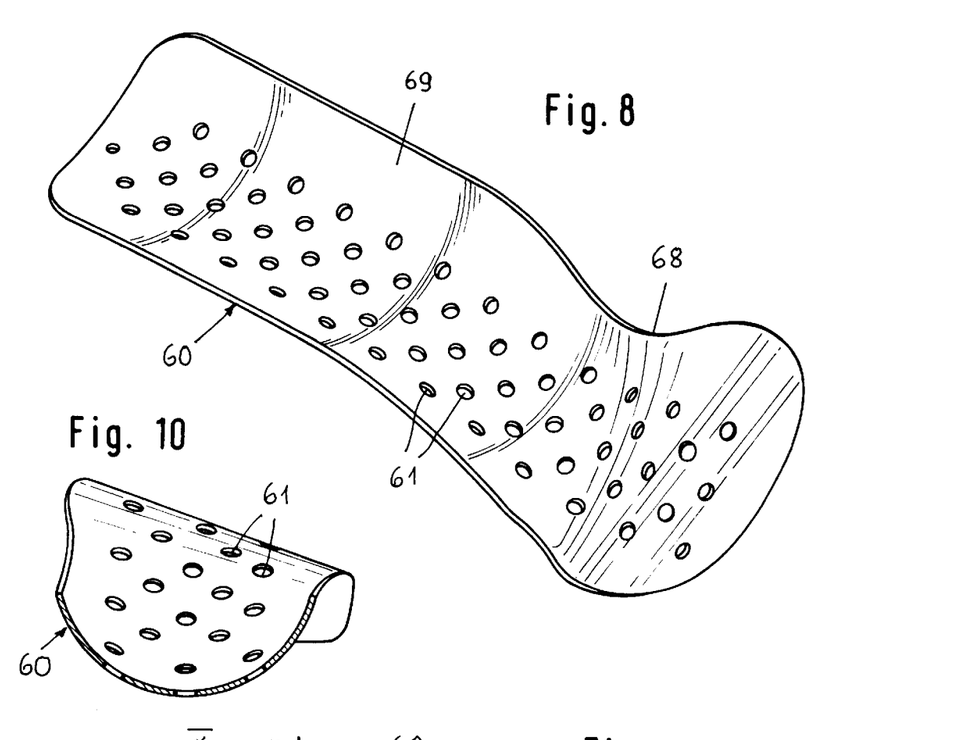
FIG. 8 shows a diagrammatical view of the splint.
FIG. 10 shows a vertical cross-section in the direction of line X—X in FIG. 9.
Figures 9, 11:
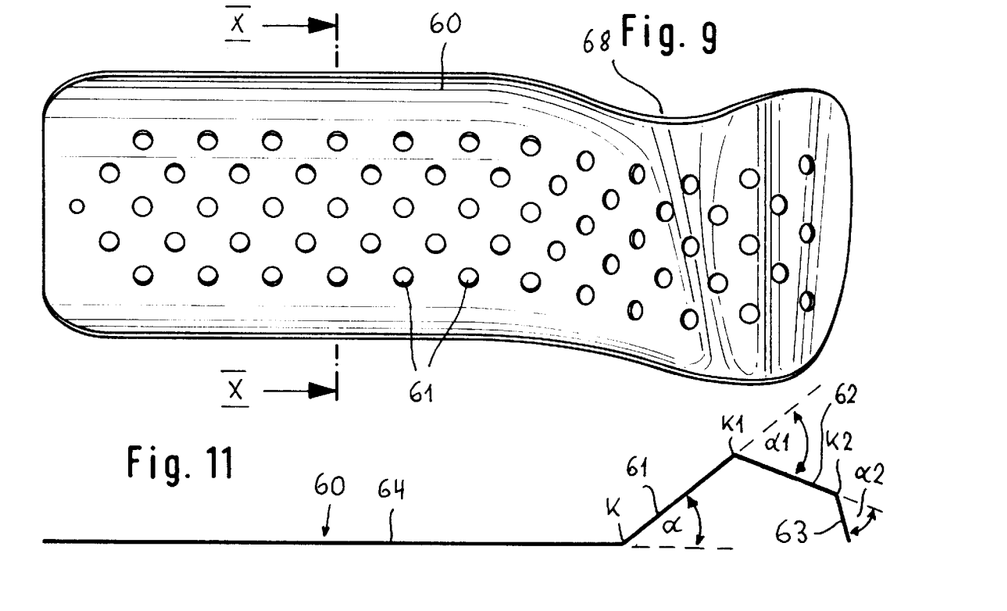
FIG. 9 shows a top view of the splint as per FIG. 8.
FIG. 11 shows a schematic longitudinal section through the splint.
Figure 12:
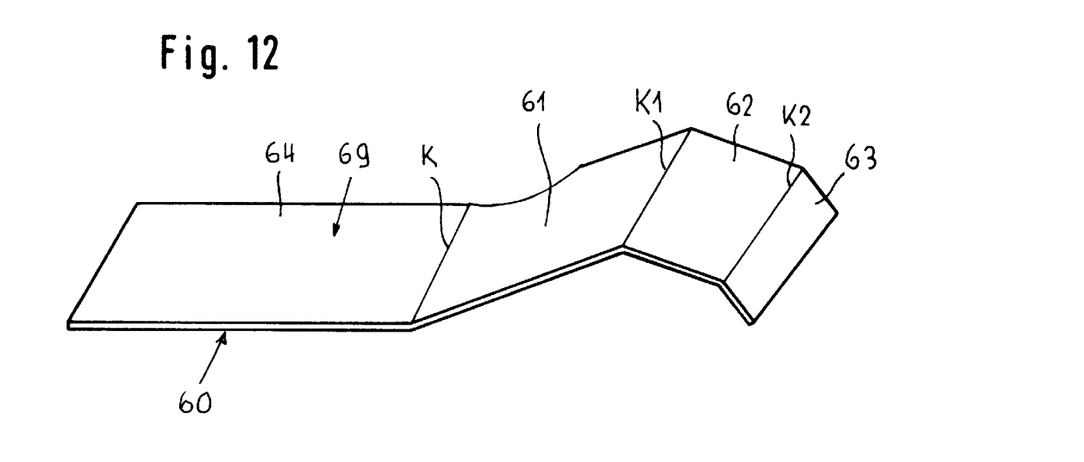
FIG. 12 shows a schematic diagrammatical view of the splint.

The splint 60 possesses, within the region of the phalanges and the metacarpal bones, three splint sections 61, 62, 63 which are bent aside towards each other (FIGS. 11 and 12) and expediently within the area of transition from the splint sleeve 69 to the splint section 61, a lateral constricted portion or indentation 68 for a lateral thumb guidance (FIGS. 8 and 12). These three reciprocally bent-aside splint sections 61, 62, 63 possess, relative to the longer splint section 64, such angular positions that an angle α between the splint sections 64, 61 comes to 40°±5° The angle α 1 between the splint sections 61, 62 comes to an angle of 60°±5° and the angles α2 between the splint sections 62, 63, comes likewise to 60°±5°. By virtue of these angular positions of the individual splint sections relative to each other, the desired angles of 40° dorsal extensions in the wrist joint HG as well as of 60° palmar flexion in the MCP and PIP joints are predetermined.

Figure 13:
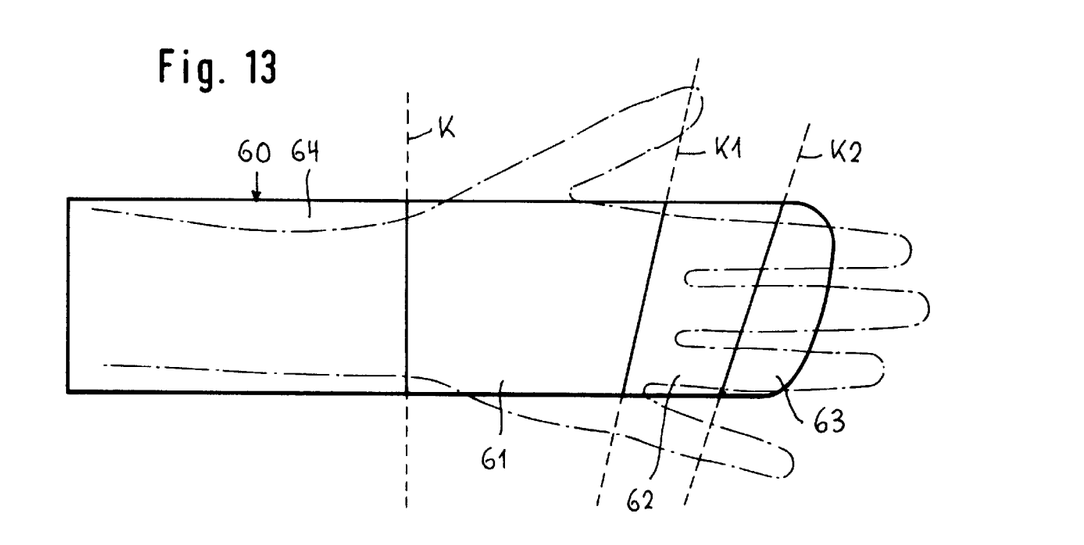
FIG. 13 shows a view from the top onto the splint with its different bending points for bending the individual splint sections.
Figure 14:
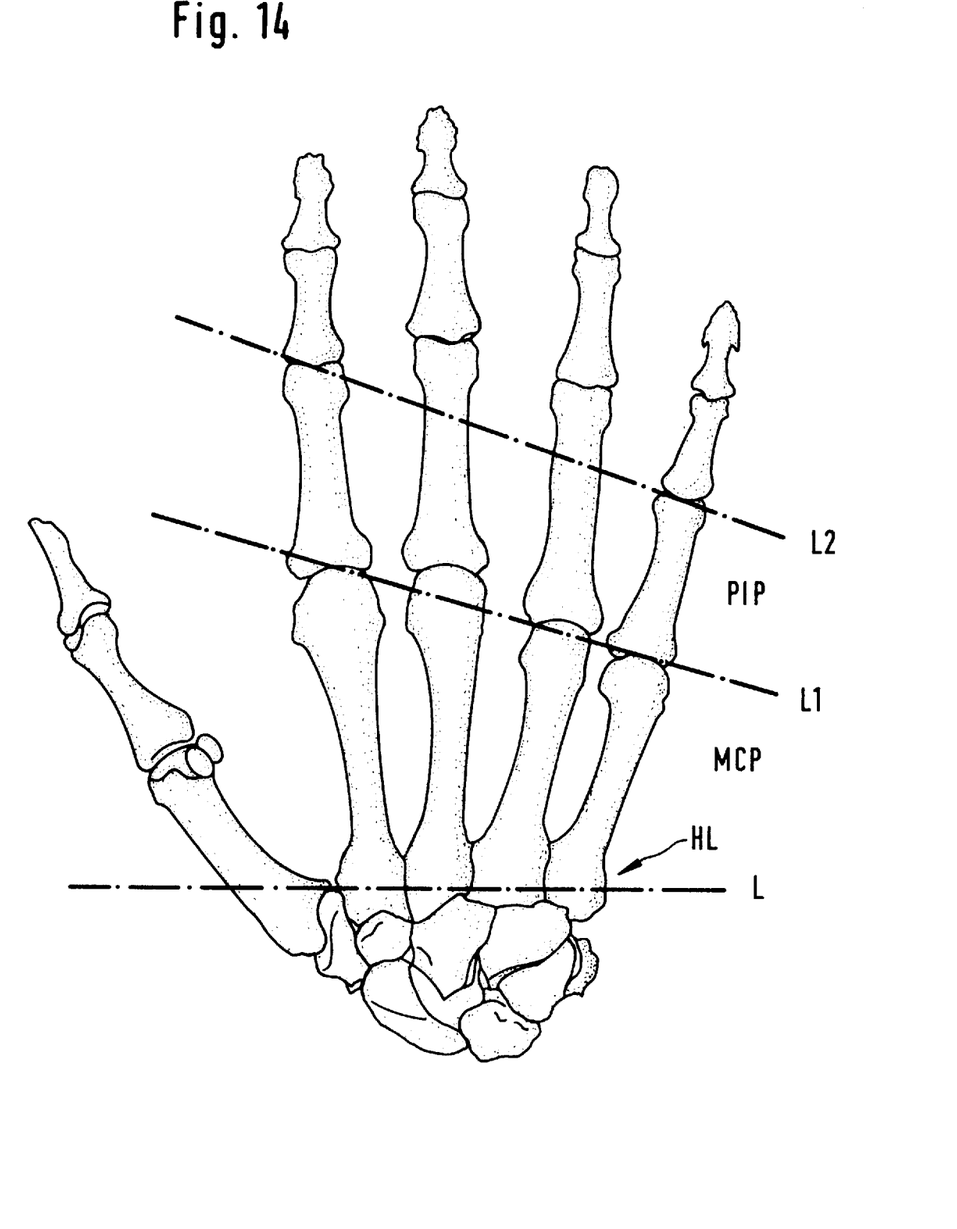
FIG. 14 shows a view of the right hand with hand and digital bones seen from the dorsal side.

Since the MCP and PIP joints of the hand do not proceed transversally to the Longitudinal direction of the forearm, but proceed obliquely (FIGS. 13 and 14), the bending lines K1, K2 between the splint sections 61, 62 and 62, 63 are preferably likewise constructed so as to proceed obliquely, whereas the bending line K between the slint sections 64, 61 of the splint 60 proceeds parallel to the longitudinal direction of the splint. The reciprocally angled sections 64, 61, 62, 63 of the splint 60 accordingly possess, in the bending lines K, K1, K2 proceeding transversally to the longitudinal direction of the splint, different angular positions and this in such a way that the bending line K, within the region of the wrist joint HG, proceeds transversally to the longitudinal direction of the splint. The bending line K1 of the splint 60 located within the region of the MCP joints proceeds corresponding to the oblique joint line L1 proceeding through the MCP joints, while the bending line K2 located within the region of the PIP joints, proceeds through the joint line L2, which is predetermined by the PIP joints (FIGS. 13 and 14). In this manner the splint 60 is adapted to the anatomical conditions of the hand.

The supporting body 10 of the orthosis 100 is expediently comprised of a heavily padded rigid fabric which, on the outside, can be provided with a washable coating or impregnation.

Figure 4:
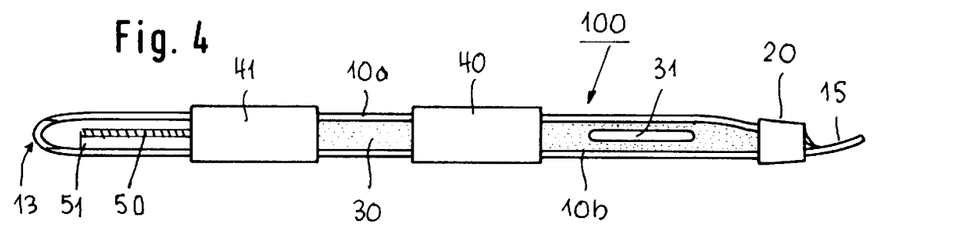
FIG. 4 shows a side view of the orthosis in a closed state by means of closing straps.
Figure 5:
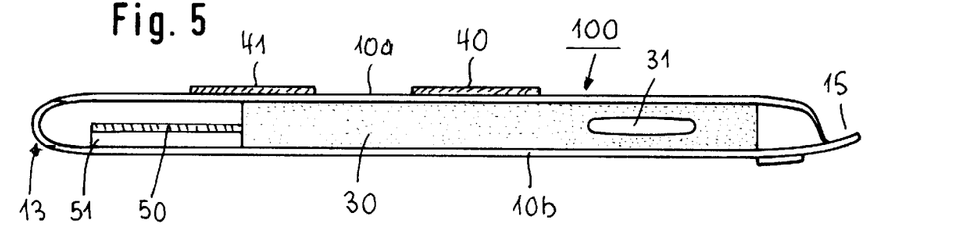
FIG. 5 shows a side view of the orthosis with the closing straps open.
Figure 6:
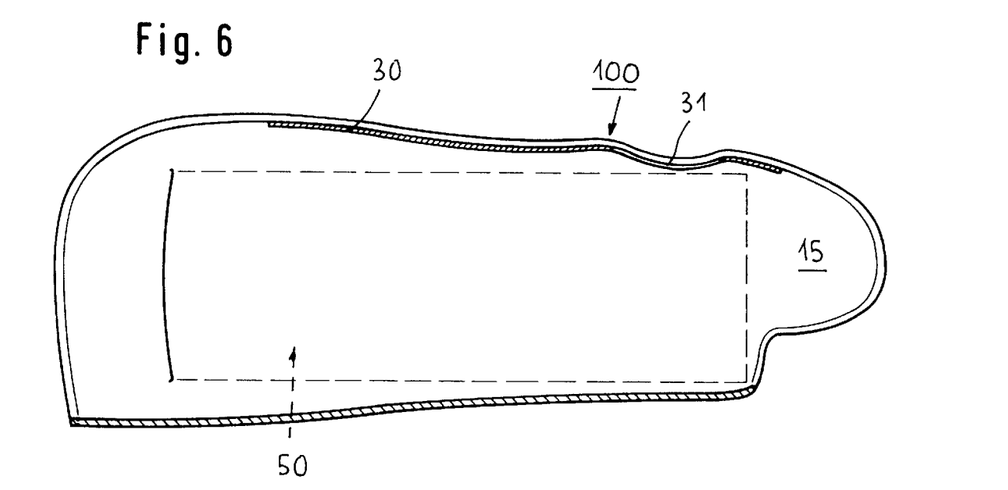
FIG. 6 shows a horizontal section through the orthosis with a pocket for the accommodation of a splint constructed on the inside.
Figure 7:
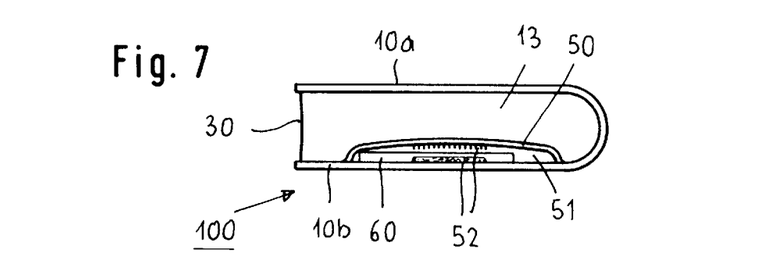
FIG. 7 shows a view upon the orthosis from the slip-in aperture with the pocket disposed on the inner wall for holding the splint.

The splint 60 is retained on one of the two inner wall areas of the supporting body 10. For this, on the inner wall area of the supporting body 10, a pocket 50 is provided, whose splint insertion aperture 51 can be closed with the aid of a closing means, such as e.g. a strip fastener 52 (FIGS. 4, 5, 6 and 7). The pocket 50 for the splint 60 is preferably attached to the inner wall area of the supporting body portion 10b (FIGS. 4 and 5). The pocket 50 is comprised of a fabric blank which is connected with the supporting body portion 10b by means of a sewn, adhesive or welded joint. A welded joint will always be made use of when e.g. the portions to be connected are comprised entirely or partially of a plastic sheeting, a fabric of plastic threads or a fabric of natural fibers coated or impregnated with a plastic. The splint 60 may be additionally provided with a padding so that no pressure is exerted upon the blood vessels located on the side of the hollow hand. Also the fabric blank forming the pocket 50 can be comprised of a padded material.

The embodiment of hand and wrist joint orthosis 100' depicted in the FIGS. 15 to 19 shows, in the basic conception, a construction corresponding to that of the orthosis 100.

In the orthosis 100', the supporting body 110 is formed by a sleeve-like blank 114 corresponding approximately to the length of the forearm so that the orthosis 100', in the applied state, extends over the entire forearm.

Figure 15:
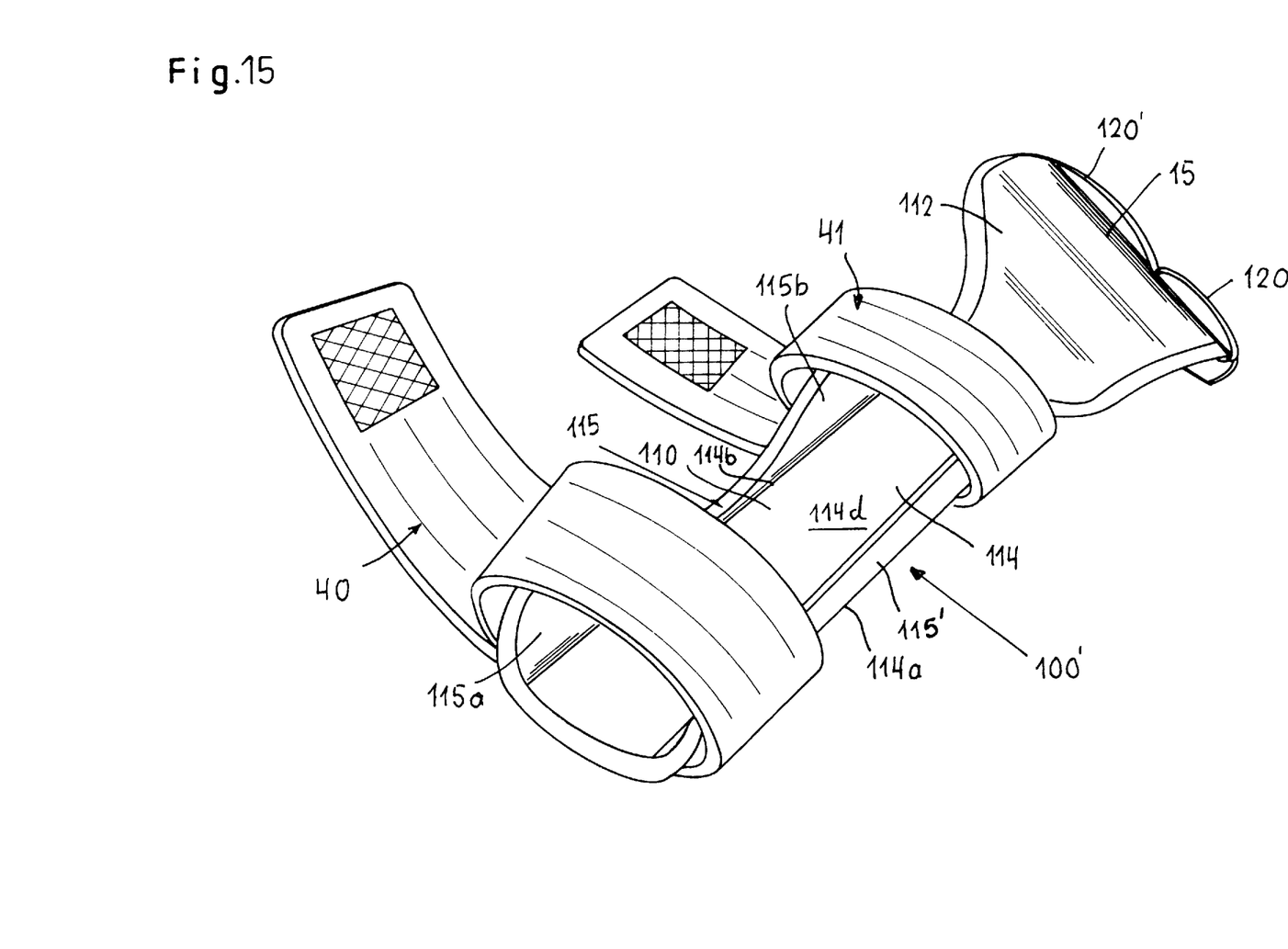
FIG. 15 shows a diagrammatical view of a further embodiment of the orthosis proceeding in the direction from the end on the forearm side to the digit-side support.
Figure 16:
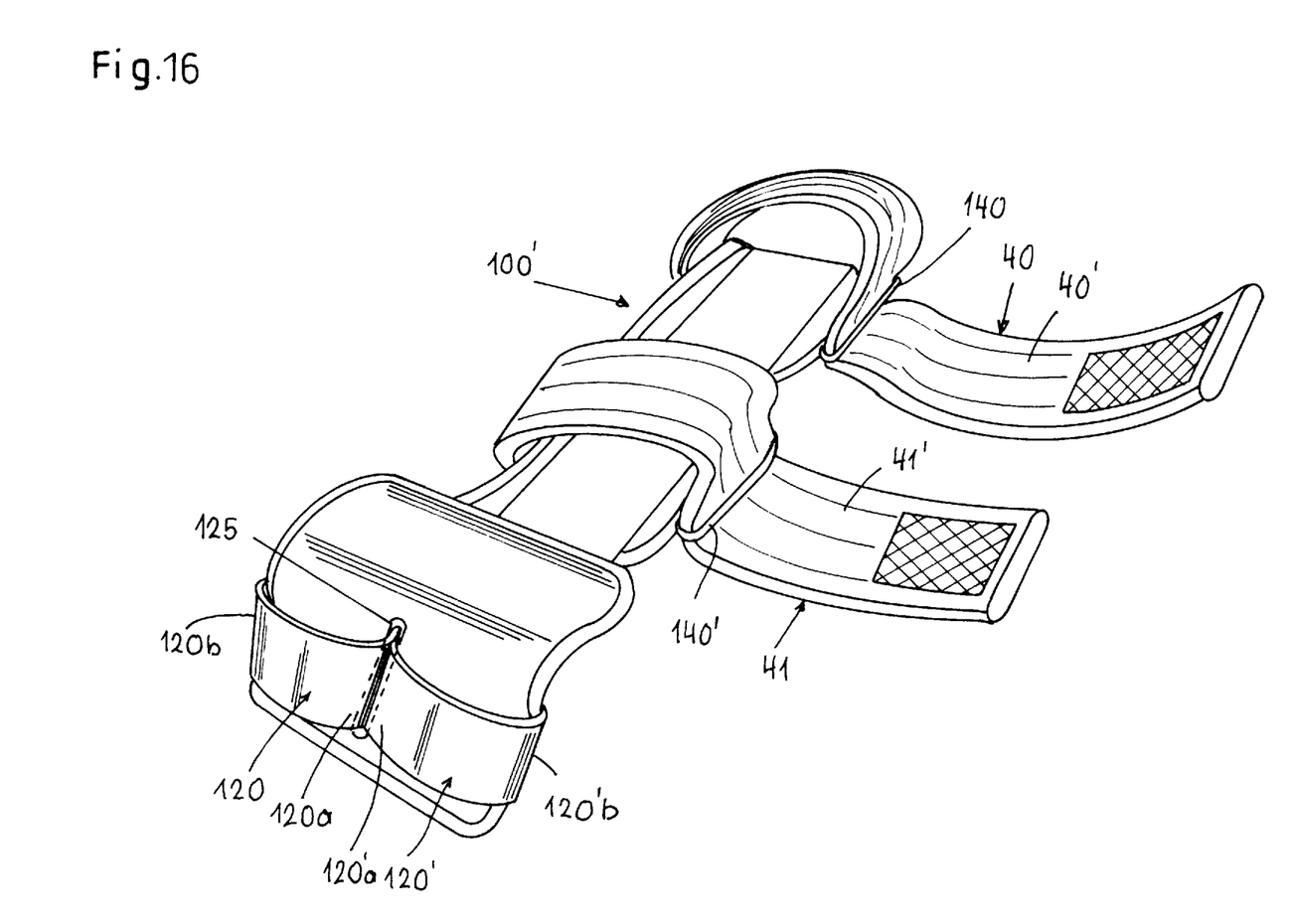
FIG. 16 shows a diagrammatical view of the orthosis as per FIG. 15 proceeding in the direction from the digit-side support to the end on the forearm side.
Figure 17:
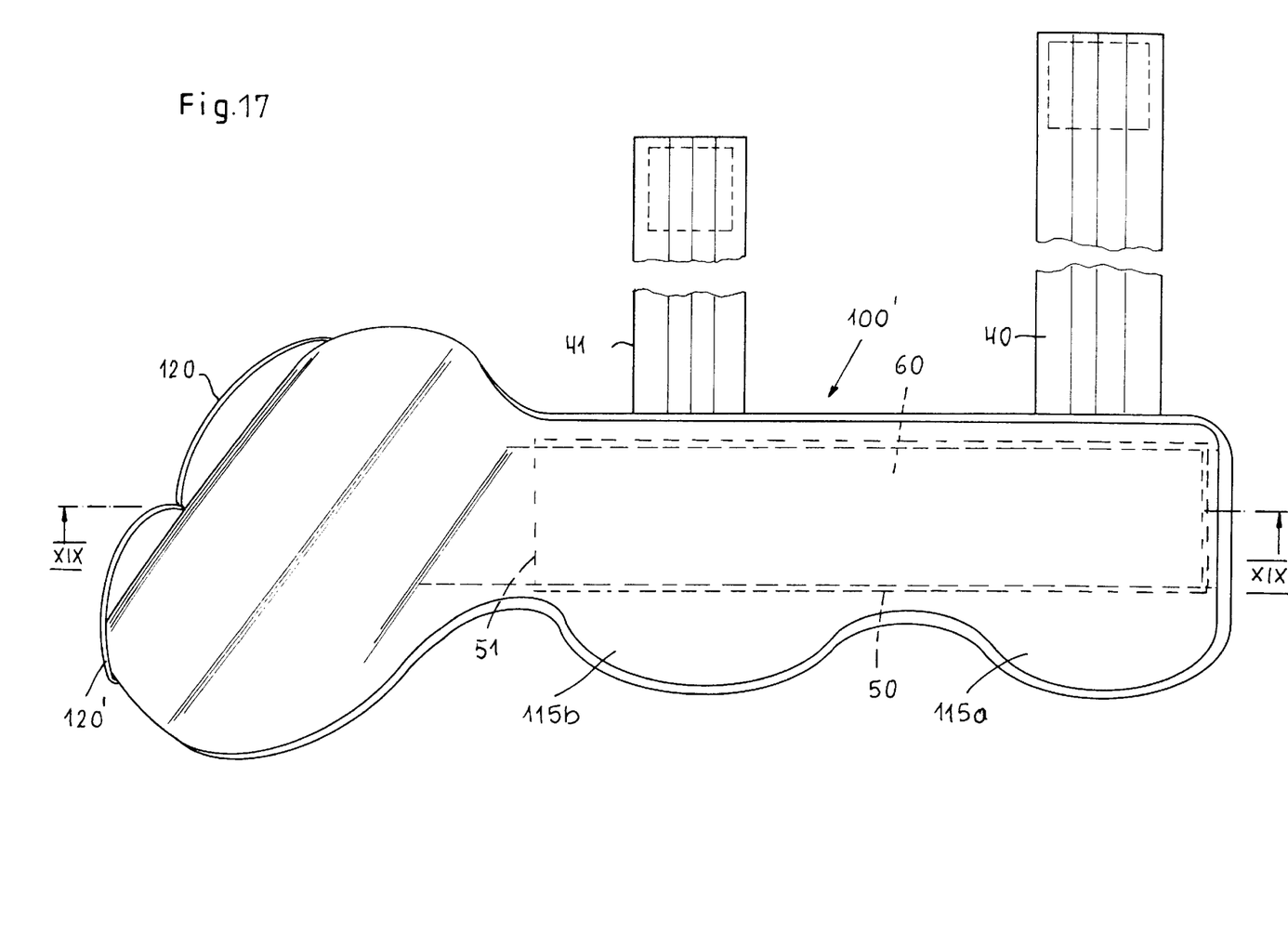
FIG. 17 shows the orthosis in a view from above.

At one end the sleeve-like blank 114 passes into a section 112 overlapping the phalanges, which terminates in the region of the proximal phalanx. The longitudinal sides 114a, 114b of the sleeve-like blank 114 possess raised marginal sections 115, 115', of which the marginal blank 115, within the area of the two closing tapes 40, 41, is provided with tab-like extensions or widenings 115a, 115b in order to obtain a lateral support and positional consolidation of the forearm when the orthosis is applied (FIGS. 15 and 16).

Figure 18:
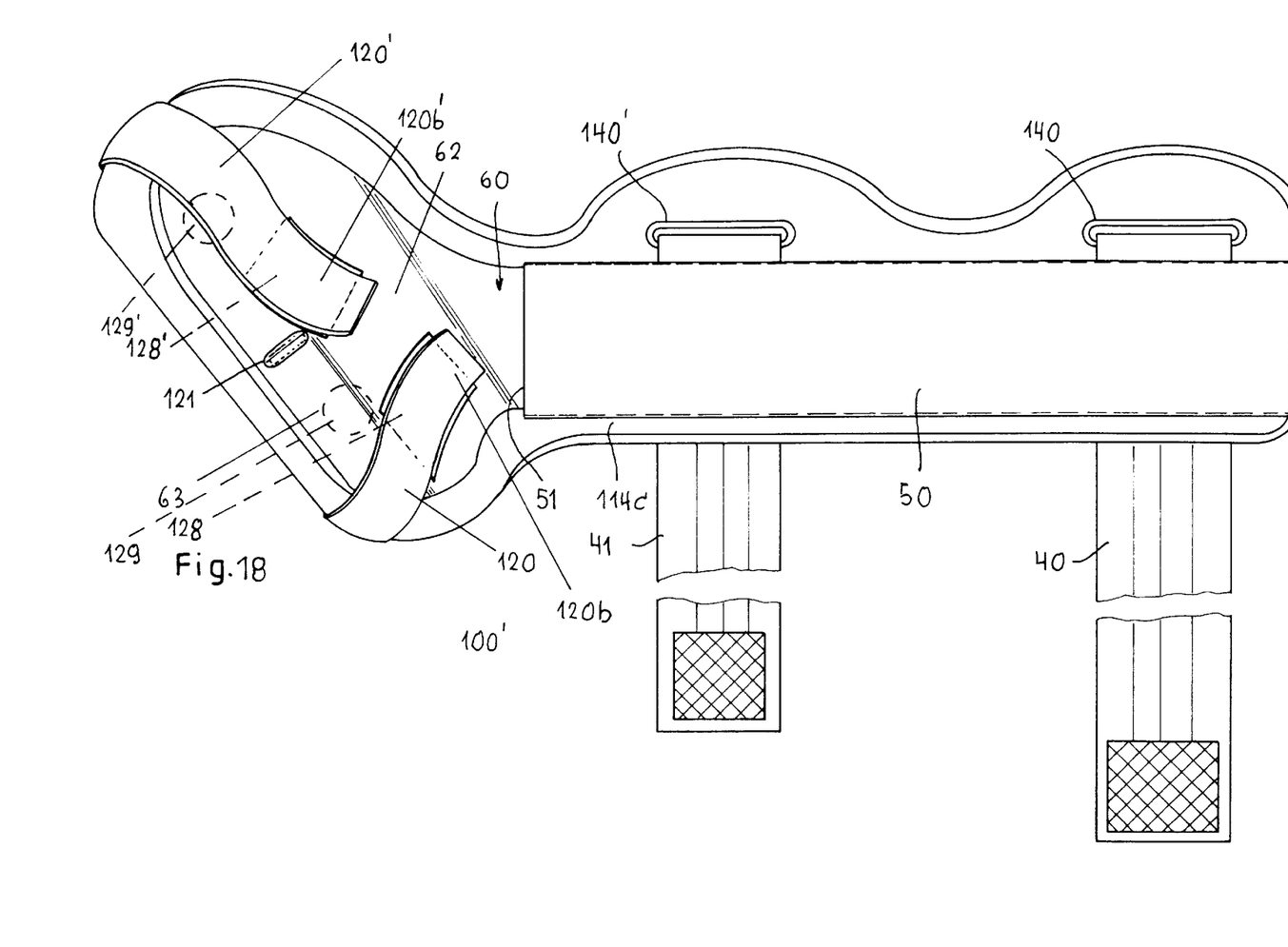
FIG. 18 shows the orthosis in a view from below.
Figure 19:
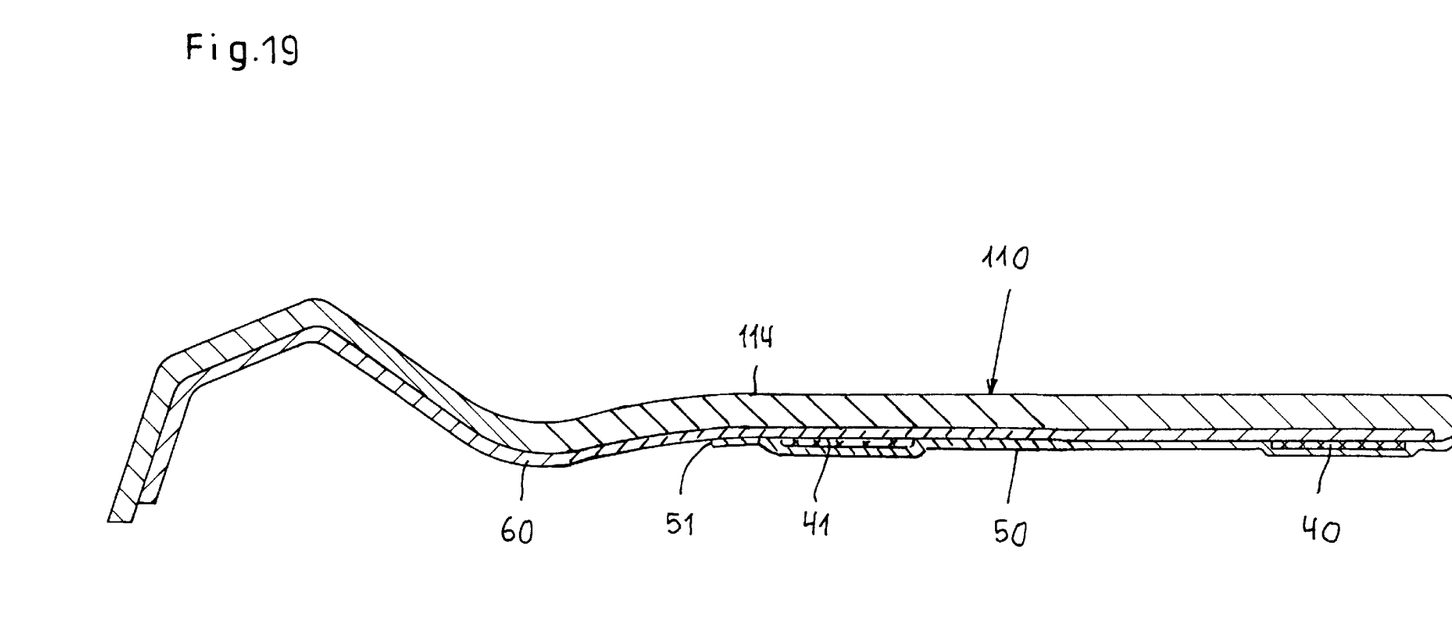
FIG. 19 shows a vertical longitudinal section in the direction of line XIX—XIX in FIG. 17.

The back 114c of the blank 114 possesses a pocket 50 provided with a splint insertion aperture 51 facing the section 112 which overlaps the phalanges, which serves for the accommodation of the splint 60. The supporting surface 114d of the blank 114 for the forearm and the phalanges is covered with a blank of a padded fabric which is advantageously provided with a washable coating or impregnation or which consists of a terry cloth-like fabric. On the interior termination 15 of the supporting body 110 or on the end of its phalanges-overlapping section 112, two inelastic digit retaining straps 120, 120' are disposed which, while following the digital contours, proceed obliquely (FIGS. 16, 17 and 18), in which case the ends 120a, 120'a are passed through a slot 125 in the external section 63 of the splint 60 and, on the rear of the splint 60, are fixed on this splint section 63 with the aid of a material thickening 121 or an otherwise constructed reinforcement (FIG. 18). The other free ends 120b, 120'b of the two straps 120, 120' are passed across the external edges of the splint section 63 and of the splint section 62 and, with the aid of Velcro strip fastener connections 128, 128', are detachably fastened to the rear of the splint section 62 so that, by means of these connections 128, 128', the length of the two straps 120, 120' is variable and adaptable to the respective digital thicknesses. The two connections 128, 128' are provided on the splint section 62 (FIG. 18).

The supporting body 110 possesses a certain flexural elasticity, i.e. it is comprised of a flexible padded fabric blank, which receives its rigidity through the splint 60 inserted into the pocket 50. A raising of the free end of the blank 114 is prevented in that the end of the blank is retained on the exterior of the splint section 63 with the aid of one or two connections 129, 129' (FIG. 18).

Each closing tape 40, 41 is comprised of a buckle 140, 140' secured to the border of the blank 114 and a tape-like blank 40', 41', which is secured to the other border of the blank 114. In the applied state of the orthosis, the closing tapes 40', 41' are passed through the buckles 140, 140' and turned down in such a way that their ends come to rest on the closing tape sections which are located between the attachment area of the closing tapes 40', 41' and the buckles 140, 140'. The ends of the closing tapes 40', 41' form, together with the material of the closing tapes 40', 41', the strip fasteners, in which case the one portion of the strip fastener is formed on the closing tape ends, while the other portion of the strip fastener is formed by the closing tape material.

We claim:

1. A hand and wrist joint orthosis comprising a supporting body adapted to be held at the hand and wrist of the user, the supporting body comprising a volar rigid splint adapted to support the hollow hand and for holding the hand and the digits in a functional position, the rigid splint being positionable so as to face the digits with a section and to terminate so as to overlap the joints within the region of the phalanges and to extend over a greater portion of the digits, the rigid splint having a longitudinal direction and comprising, so as to be positionable in the region of the phalanges and the metacarpal bones, a first splint section, a second splint section and a third splint section, wherein a first bending line positionable within the region of the wrist joint between the rigid splint and the first splint section extends transversely of the longitudinal direction of the splint, a second bending line positionable in the region of the metacarpal joints between the first and second splint sections extending corresponding to a joint line through the metacarpal joints obliquely relative to the longitudinal direction of the rigid splint, and a third bending line positionable within the region of the phalangeal joints between the second and third splint sections extending corresponding to a joint line through the phalangeal joints obliquely relative to the longitudinal direction of the rigid splint, whereby the splint sections are positioned to coincide with the joint lines, and wherein an angle between the longitudinal direction of the rigid splint and the first splint section is 40°±5°, an angle between the first and second rail sections is 60°±5° and an angle between the second and third rail sections is 60°±5°; and wherein the supporting body is a profile-sewn supporting body adapted to enclose wrist joint and hand in a sleeve-like fashion, the rigid splint being spoon-shaped and positionable on the volar side on an inner wall area of the supporting body so as to facilitate an intrinsic-plus position, the supporting body being of open construction and extending on one side in the longitudinal direction so as to form a putting-on aperture extending over the entire length of the orthosis, the supporting body comprising two body portions and adjustable closing tapes for holding together the two supporting body portions, further comprising a sleeve held by the adjustable closing tapes and extending over a length corresponding to the length of the forearm.

2. The hand and wrist joint orthosis according to claim 1, wherein the supporting body has an interior termination shaped so as to follow the anatomical contours of the digits such that a laterally located area as compared to a centrally located area is located further back and chamfered.

3. The hand and wrist joint orthosis according to claim 1, further comprising an inelastic strap adapted to fixate the digits, the inelastic strap being positionable so as be located with fixation points at a distance from a front end of the orthosis.

4. The hand and wrist joint orthosis according to claim 1, further comprising a textile insert of a fabric having a sewn-in thumb aperture for interconnecting the two supporting body portions and extending over at least a portion of the length of the supporting body, the textile insert being located in the area of the forearm sleeve of the supporting body and adapted to be located at the front portion of the hand.

5. The hand and wrist joint orthosis according to claim 4, wherein the textile insert is of a highly elastic fabric.

6. The hand and wrist joint orthosis according to claim 1, wherein the adjustable closing tapes are inelastic hook and loop-type strip fasteners with alternately oppositely directed winding directions.

7. The hand and wrist joint orthosis according to claim 1, wherein the supporting body has on an inner wall area thereof a pocket for receiving the rigid splint, the pocket having a splint insertion aperture, further comprising means for closing the splint insertion aperture.

8. The hand and wrist joint orthosis according to claim 7, wherein the closing means is a hook and loop-type fastener.

9. The hand and wrist joint orthosis according to claim 1, wherein the supporting body comprises a sleeve-like blank adapted to correspond approximately to the length of the forearm, wherein, in the section overlapping the phalanges and terminating within the region of the proximal phalanx, longitudinal sides of the blank have raised marginal sections, tab-like extensions being provided at the raised marginal sections located within areas of the two closing tapes, the supporting body further having on a rear side thereof a pocket with an insertion aperture for receiving the splint.

10. The hand and wrist joint orthosis according to claim 9, comprising two inelastic digit retention straps mounted at an interior termination of the supporting body, the digit retention straps being positionable so as to extend obliquely following the anatomical contours of the digits, the digit retention straps having first ends extending through a slot in an external section of the splint and being fixed on a rear side of the splint on the external section through a material thickening, wherein second free ends of the two straps extend across external edges of the external section and the second splint section and are detachably fastened to a rear side of the second splint section through hook and loop-type connecting means.

11. The hand and wrist joint orthosis according to claim 9, wherein the supporting body is comprised of a flexible padded fabric blank, the fabric blank being rigid when the splint is inserted into the pocket on the rear of the supporting body.

12. The hand and wrist joint orthosis according to claim 9, comprising one or two hook and loop-type strip fasteners for holding the free end of the section overlapping the phalanges of the blank of the supporting body on an outer side of the third splint section.

13. The hand and wrist joint orthosis according to claim 1, wherein each adjustable closing tape is comprised of a buckle secured to a border of the blank, and wherein each closing tape further comprises a tape-like blank, wherein, in an applied state of the orthosis, the tape-like blank rests on the blank sections located between the detachment area of the tape-like blank and the buckles, wherein ends of the tape-like blanks are retained on the tape-like blanks through hook and loop-type fasteners.

14. The hand and wrist joint orthosis according to claim 1, wherein the supporting body is comprised of a padded, rigid fabric.

* * * * *